United States Patent [19]

Yasuda et al.

[11] Patent Number: 4,465,631

[45] Date of Patent: Aug. 14, 1984

[54] 5-SUBSTITUTED-3-ISOXAZOLECARBOXYLIC ACID DERIVATIVES

[75] Inventors: Naohiko Yasuda, Yokosuka; Hisao Iwagami, Kawasaki; Eiji Nakanishi, Kawasaki; Yukio Sasaki, Kawasaki; Shigeru Yamanaka, Yokohama, all of Japan

[73] Assignee: Ajinomoto Company, Incorporated, Tokyo, Japan

[21] Appl. No.: 482,544

[22] Filed: Apr. 6, 1983

[30] Foreign Application Priority Data

Apr. 12, 1982 [JP] Japan .................................. 57-59611

[51] Int. Cl.$^3$ ................. C07D 499/68; C07D 499/70; C07D 501/22; C07D 501/44
[52] U.S. Cl. ................................ 260/239.1; 424/246; 424/263; 424/271; 544/22; 544/25; 544/27; 544/28; 544/30
[58] Field of Search ................. 260/239.1; 544/22, 27, 544/28, 25, 30; 424/246, 263, 271

[56] References Cited

U.S. PATENT DOCUMENTS

| | | | |
|---|---|---|---|
| 3,939,149 | 2/1976 | Konig et al. | 260/239.1 |
| 3,959,258 | 5/1976 | Konig et al. | 260/239.1 |
| 4,217,450 | 8/1980 | Yasuda et al. | 544/25 |

Primary Examiner—Natalie Trousof
Assistant Examiner—Vera C. Clarke
Attorney, Agent, or Firm—Oblon, Fisher, Spivak, McClelland & Maier

[57] ABSTRACT

A 5-substituted-3-isoxazolecarboxylic acid derivative of the general formula:

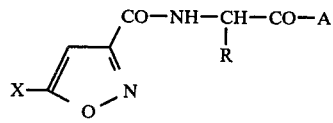

wherein X stands for a phenyl group, thienyl group, furyl group or pyridyl group, each of which optionally may carry at least one substituent group; R stands for a phenyl group or hydroxyphenyl group; and A stands for a group of the formula:

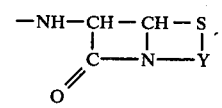

wherein Y stands for

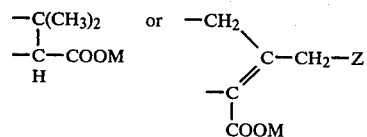

in which the carbon atom with which the carboxyl group combines with the nitrogen atom in A, M stands for a hydrogen atom or a substituent group, and Z stands for a hydrogen atom, hydroxy group, acyloxy group, carbamoyloxy group, aromatic heterocycle thio group or aromatic nitrogen-containing heterocycle quaternary ammonium group, is disclosed along with methods for producing these compounds.

12 Claims, No Drawings

5-SUBSTITUTED-3-ISOXAZOLECARBOXYLIC ACID DERIVATIVES

The present invention relates to novel 5-substituted-3-isoxazolecarboxylic acid derivatives, which can be used as antibiotics for treating infectious diseases of human beings and animals caused by Gram-positive bacteria; Gram-negative bacteria, especially glucose non-fermentative Gram-negative rods; and anaerobic bacteria.

The present inventors have completed the present invention by succeeding in the synthesis of novel 5-substituted-3-isoxazolecarboxylic acid derivatives, having the following general formula:

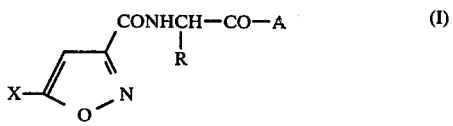

and by finding the fact that such novel compounds have a broad spectrum of antibacterial activity against Gram-positive and Gram-negative bacteria, and furthermore have a marked antibacterial activity against pseudomonas aeruginosa and another glucose non-fermentative Gram-negative rods and anaerobic bacteria, and therefore can be used as an antibiotic.

In the above mentioned general formula (I), X in any either case stands for a phenyl group, thienyl group, furyl group or pyridyl group, which may have at least one substituent group. R stands for phenyl group or hydroxyphenyl group.

In the above mentioned formula (I) when X is a group having at least one substituent group, examples of the substituent groups are, for example, a halogen atom like a chlorine atom, hydroxy group, lower alkyl group, lower alkyloxy group, amino group, acylamino group or nitro group.

Amino acids constituting 5-substituted-isoxazole-3-carboxylic acid derivatives in the present invention are, for example, α-phenylglycine (in the above mentioned formula I, R is phenyl group), and α-4-hydroxyphenylglycine (in the above mentioned R is 4-hydroxyphenyl group), which may be in the L-form, D-form or DL-form.

In view of antibacterial activity, in many cases, the D-form is suitable.

In the above mentioned general formula (I), A stands for a group shown by the following general formula:

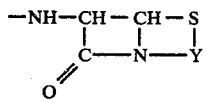

wherein Y stands for

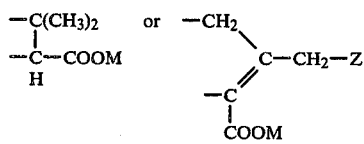

The carbon atom with which the carboxyl group combines combines with the nitrogen atom in A, M stands for a hydrogen atom or a non-toxic substituent group, and Z stands for a hydrogen atom, hydroxy group, acyloxy group, carbamoyloxy group, aromatic heterocycle-thio group, or aromatic nitrogen-containing heterocycle quarternary ammonium group.)

An example of the acyloxy groups is acetoxy group. Examples of aromatic heterocycle-thio group are 5-(1-methyltetrazolyl)thio group and 2-(1,3,4-thiadiazolyl)thio group. Examples of the aromatic nitrogen-containing heterocycle tert-ammonium groups are pyridinium, quinolinium, picolinium, which may have at least are substituent group.

5-Substituted-isoxazole-3-carboxylic acid derivatives in the present invention involve the derivative of the above mentioned formula (I) wherein the hydrogen atom of the carboxyl group in Y is substituted with a metal such as sodium, potassium, calcium, aluminum, or an ammonium such as triethylammonium, procaine, dibenzylammonium, N-benzyl-β-phenethylammonium. Namely, the derivative is in the salt form, or is in the hydrate form. Of course, in this case a pharmaceutically non-toxic substituent group is employed.

So far, it has known that Penicillins carrying an amino group in the α-position and cephalosporins shown by the general formula,

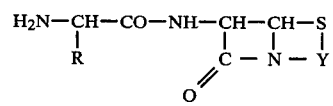

wherein R and Y, respectively, have the same meanings as above, show an antibacterial activity against not only Gram-positive bacteria but also Gram-negative bacteria. However, they have the following weak point. They do not have an effective antibacterial activity against *Pseudomonas aeruginosa* and other glucose non-fermentative Gram-negative rods and anaerobic bacteria causing clinically serious infectious diseases of human beings and animals.

The above mentioned 5-substituted-isoxazole-3-carboxylic acid derivatives in the present invention have a broad spectrum of antibacterial activity against Gram-positive and Gram-negative bacteria, and furthermore have a marked antibacterial activity against *Pseudomonas aeruginosa* and other glucose non-fermentative Gram-negative rods and anaerobic bacteria, and therefore are compounds for practical use.

In order to produce the object compounds of the present invention, for example, the α-aminopenicillins and cephalosporins shown by the general formula,

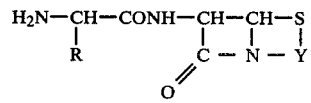

are reacted with 5-substituted-isoxazole-3-carboxylic acids shown by the general formula,

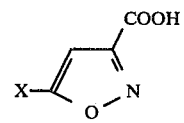

or the reactive acid derivatives thereof by condensation, or the penicillins and cephalosporins shown by the general formula,

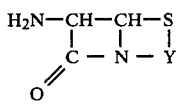

are reacted with 5-substituted-isoxazole-3-carboxylic acids shown by the general formula,

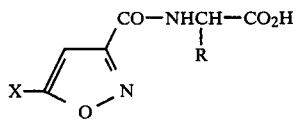

or the reactive acid derivatives thereof by condensation.

For the above condensation reaction, the condensation reaction which is known as it is can be employed. Now, R, X and Y are the same as prescribed before.

Examples of suitable reactive acid derivatives are acid halides, mixed anhydrides, activated amido, and activated ester. Especially, acid chloride, acid azide, dialkylphosphoric acid mixed anhydride, phenylphosphoric acid mixed anhydride, diphenylphosphoric acid mixed anhydride, dibenzylphosphoric acid mixed anhydride, halogenized phosphoric acid mixed anhydride, dialkylphosphorous acid mixed anhydride, sulfurous acid mixed anhydride, thiosulfuric acid mixed anhydride, sulfuric acid mixed anhydride, alkylcarbonic acid mixed anhydride, fatty acid such as pivalic acid, pentanoic acid, isopentanoic acid, 2-ethylbutanoic acid, trichloroacetic acid, mixed anhydrides, aromatic carboxylic acids such as benzoic acid, p-methylbenzoic acid, mixed anhydride, acids anhydride, acid amides with imidazole, 4-substituted imidazole, dimethylpyrazole, triazole, tetrazole, esters such as cyanomethylester, methoxymethylester, vinylester, propargylester, p-nitrophenylester, 2,4-dinitrophenylester, trichlorophenylester, pentachlorophenylester, methane sulfonylphenylester, phenylazophenylester, phenylthioester, p-nitrophenylthioester, p-cresylthioester, carboxymethylthioester, pyranyl ester, pyridyl ester, piperidyl ester, 8-quinolilthio ester, ester with N,N-dimethylhydroxylamine, 1-hydroxy-2-(1H)-pyridone, N-hydroxy succinimide or N-hydroxy phthalimide, are used in many cases.

The reactive acid derivatives are produced as follows: For example, the acid chloride is synthesized by reacting the above mentioned 5-substituted-isoxazole-3-carboxylic acid or the derivative thereof with, for example, thionylchloride or phosphorus pentachloride. The activated ester such as 2,4-dinitrophenylester is obtained by reacting with 2,4-dinitrophenol in the presence of a condensing agent such as dicyclohexylcarbodiimide.

The reaction of the above mentioned reactive acid derivatives with the above mentioned penicillins or cephalosporins is carried out in the presence of a base such as alkali metal hydrogencarbonate, alkali metal carbonate, trialkylamine, pyridine. When a solvent is used, for example, water, acetone, dioxane, acetonitrile, chloroform, methylene chloride, tetrahydrofuran and N,N-dimethyl formamide (DMF) are employed. The hydrophilic organic solvent can be used in mixture with water. The reaction may be usually carried out under cooling or at room temperature.

In the reaction with the reactive acid derivative, it is also possible to react with the ester to which the carboxyl group in Y of the above mentioned general formula has been converted, for example, t-butylester, benzylester, silylester, trichloroethyl ester. These ester groups are removed by a conventional method after the reaction to make the carboxyl group in the free form.

The object compound of the above mentioned general formula wherein A the cephalosporin skeleton and Z is an aromatic heterocycle thio group or a quarternary ammonium group, is obtained, for example, by synthesizing cephalosporins wherein Z is acetoxy group, and thereafter substituting the acetoxy group with the aromatic heterocycle thio group or the quarternary ammonium group, too.

Regarding the object compound of the above mentioned general formula wherein a substituent group of X is the substituent group such as amino group and acyl amino group, the object compound having amino group as the substituent group is obtained, for example, by synthesizing penicillins or cephalosporins having a nitro group as the substituent group, and thereafter reducing it in the presence of a catalyst. Further, by acylating the amino group of the compound as produced above with an acylating agent such as an acyl halide, the object compound having an acylamino group as the substituent group is obtained.

The reaction product may be isolated by using the conventional isolating methods such as extraction, column chromatography, recrystallization.

Thus obtained 5-substituted-isoxazole-3-carboxylic acid derivative is converted to a non-toxic salt such as alkali metal salt, ammonium salt, and further organic base salt by a conventional salt-forming method. These salts are preferable in view of drug preparation, for example, since they can be dissolved in water.

The present invention will be explained by the following examples further in details.

EXAMPLE 1

A mixture of 5-(4-methylphenyl)-3-isoxazolecarboxylic acid (0.97 g, 5 m mole) and thionyl chloride (10 ml) was stirred at 80° C. for 4 hours. After evaporating the mixture, dry benzene (10 ml) was added and the mixture was concentrated in vacuo again to give the corresponding acid chloride as the residue. This residue was dissolved in dry acetonitrile (15 ml).

Ampicillin trihydrate (1.81 g, 4.5 m mole) was suspended in a mixture of water (25 ml) and acetonitrile (10 ml), and the pH of the suspension was adjusted carefully to 8.5 with 2N-NaOH under ice-cooling. To this solution, the acid chloride solution previously prepared was added dropwise with stirring and ice-cooling. After addition, the solution was stirred for 1 hour under ice-cooling and for 1 hour at room temperature. During the reaction, the pH of the mixture was kept at 7.5~8.0 with 2N-NaOH and 2N-HCl. After adding water (15 ml), the mixture was evaporated in vacuo under 30° C. in order to remove acetonitrile. The water solution was covered with ethylacetate (100 ml) and the pH of the water phase was brought to 1.5 with 2N-HCl. Organic layer was separated and the water layer was extracted by ethyl acetate (100 ml). The combined organic layer was dried and evaporated to a syrup in vacuo. The residue was triturated with a mixture of etherpetroether (1:1). The triturated material was collected by filtration and dried under vacuum to give 1.6 g of α-[5-(4-methylphenyl)-3-isoxazolecarboxamido]-benzylpenicillin; IR (Nujol): 1780 cm$^{-1}$ (β-lactam); NMR (DMSO-d$_6$): δ 1.44 (3H,S,—CH$_3$), 1.55 (3H,S,—CH$_3$), 2.36 (3H, S, CH$_3$—Ph), 4.20 (1H, S, C$_3$—H), 5.30~6.06 (3H, m, C$_5$—H, C$_6$—H and Ph—CH—CO), 6.75 (2H, d,

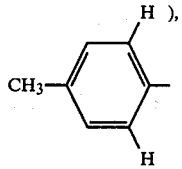

δ 7.17~7.60 (8H, m, Ph—H,

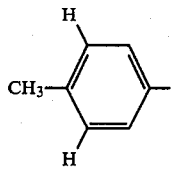

and isoxazole C$_4$—H).

The desired compounds of the present invention were synthesized in the same method as in Example 1. The results were shown in Table 1.

was concentrated in vacuo again to give a solid material.

As the residue the thus obtained 5-(m-anisyl)-isoxazole-3-carboxylic acid chloride was dissolved in acetonitrile (48 ml).

On the other hand, 7β-[D(−)-(α-amino)-phenylacetoamide]-3-acetoxymethyl-3-cephem-4-carboxylic acid (5.5 g, 13.6 m mole) was suspended in a mixture of water (70 ml) and acetonitrile (34 ml) under ice-cooling. 2N-NaOH was added dropwise thereto to make the mixture a homogeneous solution. The pH value of the solution was 8.5. To this solution, the acid chloride acetonitrile solution previously prepared was added dropwise with stirring and ice-cooling. During the reaction, the pH of the mixture was kept at 7.5~8.0 with 6%-HCl and sodium hydrogencarbonate saturated aqueous solution.

After the reaction, to the reaction solution water (35 ml) was added and then acetonitrile was distilled off in vacuo and at not more than 30° C. The remaining aqueous solution was washed with ethyl acetate (180 ml). To the residual aqueous solution ethyl acetate (230 ml) was added and then 6% HCl was added dropwise thereto while stirring to make the pH value of the water layer 2.0. The ethyl acetate layer was separated. The aqueous layer was extracted again with ethyl acetate (100 ml). The two ethyl acetate layers were combined and dried over anhydrous magnesium sulfate.

The ethyl acetate solution was concentrated at not more than 30° C. and to thus obtained residue ethyl ether was added to make a powdered material. Thus

TABLE 1

| Example No. | Object Compound | IR (cm$^{-1}$) $\nu_{c=o}$ (β-lactam) | NMR δ value; solvent |
|---|---|---|---|
| 2 | D-α-(5-phenylisoxazole-3-carboxamido)-benzylpenicillin sodium salt | 1770 | |
| 3 | D-α-(5-m-anisylisoxazole-3-carboxamido)-benzylpenicillin sodium salt | 1767 | 1.40(S,3H), 1.49(S,3H) 3.78(S,3H), 3.90(S,1H) 5.20~5.50(m,2H) 5.87(d,1H), 6.80~7.60 (m,1CH); DMSO—d$_6$ |
| 4 | D-α-(5-m-nitrophenylisoxazole-3-carboxamido)-benzyl-pencillin sodium salt | 1770 | |
| 5 | D-α-(5-p-methylphenyl-isoxazole-3-carboxamido)-p-hydroxybenzylpenicillin sodium salt | 1775 | 1.42(S,3H), 1.52(S,3H) 2.33(S,3H), 3.88(S,1H) 5.22~5.53(m2H) 5.72(d,1H), 6.68(d,2H); DMSO—d$_6$ |
| 7 | D-α-[5-(2-pyridyl)-isoxazole-3-carboxamido]-benzyl-penicillin sodium salt | 1770 | |
| 8 | D-α-[5-(2-thienyl)-isoxazole-3-carboxamido]-benzyl-penicillin sodium salt | 1773 | |
| 9 | D-α-(5-m-chlorophenyl-isoxazole-3-carboxyamido) benzylpenicillin | 1780 | |
| 10 | D-α-(5-m-aminophenyl-isoxazole-3-carboxamido)-benzylpenicillin | 1780 | |

EXAMPLE 11

A mixture of 5-(m-anisyl)-isoxazole-3-carboxylic acid (2.70 g, 12.3 m mole) and thionyl chloride (25 ml) was stirred while heating at 80° C. for 2 hours. After completion of the reaction, the solution was concentrated in vacuo to remove thionyl chloride. To the thus obtained residue dry benzene (25 ml) was added and the mixture obtained solid material was placed on filter paper and dried to obtain an object product, 7β-[D-(−)-α-(5-(m-anisyl)-isoxazole-3-carboxamido)-α-phenylacetamido]-cephalosporanic acid (4.59 g, 7.57 m mole; yield: 61.5%).

The above mentioned product was added to a mixture of methanol (60 ml) and ethyl acetate (60 ml), and then to the mixture while stirring at room temperature. Sodium 2-ethyl hexanoate n-butanol solution (2M/l, 4.46 ml) was added and stirred for 15 minutes. This solution was allowed to stand with ice-cooling for 4 hours to precipitate a solid material. Thus obtained solid material was placed on filter paper and dried to obtain the object product, 7β-[D(−)-α-(5-(m-anizyl)isoxazole-3-carboxamido)-α-phenylacetoamido]cephalosporanic acid sodium salt (4.44 g, 7.07 m mole; yield: 93.4%).

IR spectrum (nujole):
$v_{c=o}$ (β-lactam) = 1760 cm$^{-1}$
$v_{c=o}$ (β-lactam) = 1775 cm$^{-1}$ $v_{c=o}$ (OCCH$_3$) = 1725 cm$^{-1}$ NMR spectrum (solvent: DMSO)

δ 1.97 (S, 3H)      (H$_3$CCO−)

3.08~3.48 (dd, 2H)  (−CH$_2$−(2-position))

3.82 (S, 3H)        (H$_3$CO−⟨○⟩−)

4.62~5.15 (dd, 2H)  (−CH$_2$−OCCH$_3$)

5.35~5.98 (m, 3H)   (CH−⟨○⟩−, −H (6-position), −H (7-position))

6.95~7.60 (m, 10H)  (arom)

EXAMPLE 12

7β-[D(−)-α-(5-(m-anisyl)-isoxazolyl-3-carboxamido]cephalosporanic acid sodium salt as prepared in Example 11 (1.26 g, 2.0 m mole) was dissolved in phosphate buffer (20 ml, pH 6.4) and 1-methyl-5-mercapto-1H-tetrazole (258 mg, 2.22 m mole) was added thereto. In such case the pH value thereof fell and the pH value was adjusted to 6.4 with 2N-NaOH. This solution was reacted at 60° C. for 24 hours while stirring. After 5-hours reaction, the pH value was adjusted to 6.5 with 2N-NaOH. After completion of the reaction, to the reaction solution water (40 ml) was added and an insoluble material was separated by filtration. To the filtrate with ice-cooling 2N-NaOH was added to adjust the pH value to 7.0 and the mixture was washed with ethyl acetate (60 ml). To the aqueous layer ethyl acetate (100 ml) was added and 6% HCl was added thereto while stirring to adjust the pH value to 2. An insoluble material was removed by filtration, and thereby the solution having 2 layers was made. An aqueous layer was extracted again with ethyl acetate (100 ml). The ethyl acetate layers were combined, washed with water, dried over anhydrous magnesium sulfate, and concentrated. To the residue ethyl ether was added to powder it. The powdered material was placed on filter paper and obtain the object product, 7β-[D(−)-α-(5-(m-anisyl)-isoxazole-3-carboxamido)-α-phenylacetamido]-3-(1-methyl-1H-tetrazole-5-yl)thiomethyl-3-cephem-4-carboxylic acid (315 mg, yield: 25.0%). This product was converted to a sodium salt in the same manner as in Example 11.

IR spectrum (Nujole): $v_{c=o}$(β-lactam)=1780 cm$^{-1}$

EXAMPLE 13

7β-[D(−)-α-(5-(2-thienyl)-isoxazole-3-carboxamido)-α-phenylacetamido]-3-acetoxymethyl-3-cephem-4-carboxylic acid sodium salt was produced in the same manner as in Example 11.

IR spectrum (Nujole): ν

EXAMPLE 14

Isonicotinamide (244 mg, 2 mM) and potassium iodide (8.3 g) were dissolved in water (11 ml), and then 7β-[D(−)-α-(5-(2-thienyl)-isoxazole-3-carboxamido)-α-phenyl-acetamido]-3-acetoxymethyl-3-cephem-4-carboxylic acid sodium salt as synthesized in Example 13 (582 mg) was added thereto. The mixture was stirred while heating at 70° C. for 2 hours. After reaction, the reaction solution was cooled and as it is treated with "XAD-2" produced by Rhöm & Haas Co. (500 ml). The object product was eluted with water. The fractions containing the object product were collected and freeze-dried to obtain 7β-[D(−)-α-(5-(2-thienyl)-isoxazole-3-carboxamido)-α-phenyl-acetamido]-3-(4-carbamoyl-pyridinium)methyl-3-cephem-4-carboxylate (4 mg).

IR spectrum (Nujol): $v_{c=o}$(β-lactam)=1767 cm$^{-1}$

Regarding the products produced in the above mentioned Examples antibacterial activities against some microorganisms were obtained. Some of them were listed in Table 2.

TABLE 2

| Antibacterial Activity | | | |
| --- | --- | --- | --- |
| | Example No. | | (MIC μg/ml) Carbenicillin (Control) |
| | 1 | 3 | 8 | |
| Staphylococcus aureus | 0.10≦ | 0.20 | 0.10≦ | 0.78 |
| Escherichia coli | 12.5 | 12.5 | 12.5 | 12.5 |
| Klebsiella pneumoniae | 6.25 | 12.5 | 12.5 | >100 |
| Proteus mirabilis | 0.78 | 0.39 | 0.78 | 0.78 |
| Serratia marcescens | 12.5 | 12.5 | 25 | >100 |
| Pseudomonas aeruginosa | 3.13 | 6.25 | 6.25 | 25 |
| Pseudomonas cepacia | 3.13 | 3.13 | 6.25 | >100 |
| Pseudomonas maltophilia | 6.25 | 12.5 | 12.5 | >100 |
| Alcaligenes faecalis | 6.25 | 6.25 | 12.5 | >100 |
| Achromobacter xylosoxidans | 1.56 | 3.13 | 3.13 | >100 |
| Bacteroides fragilis | 6.25 | 12.5 | 12.5 | >100 |

As is evident from Table 2, the spectrum of the compounds in the present invention for antibacterial activities against microorganisms is very wide and the antibacterial activities are superior to the conventional standard antibiotics. Accordingly, the present invention has remarkable effects.

What is claimed is:

1. A 5-substituted-3-isoxazolecarboxylic acid derivative of the general formula:

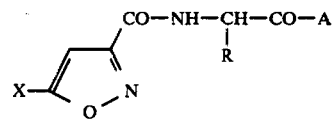

wherein X stands for a phenyl group, thienyl group, furyl group or pyridyl group, each of which optionally may carry at least one substituent group; R stands for a phenyl group or hydroxyphenyl group; and A stands for a group of the formula:

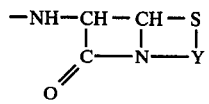

wherein Y stands for

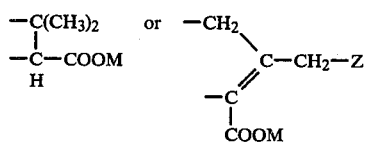

in which the carbon atom with which the carboxyl group combines combines with the nitrogen atom in A, M stands for a hydrogen atom or a substituent group, and Z stands for a hydrogen atom, hydroxy group, acyloxy group, carbamoyloxy group, aromatic heterocycle thio group or aromatic nitrogen-containing heterocycle quaternary ammonium group.

2. The derivative as set forth in claim 1 wherein the substituent group which the phenyl group carries, if any, in the formula, is a halogen atom, hydroxy group, lower alkyl group, lower alkyloxy group, amino group, acylamino group or nitro group.

3. The derivative as set forth in claim 1 wherein the amino acid constituting the derivative is in the D-form.

4. The derivative as set forth in claim 1 wherein —COOM is a pharmaceutically non-toxic salt.

5. The derivative as set forth in claim 4 wherein M is a metal ion.

6. The derivative as set forth in claim 5 wherein M is sodium, potassium, calcium, or aluminum.

7. The derivative as set forth in claim 4 wherein M is an ammonium group.

8. The derivative as set forth in claim 7 wherein M is triethylammonium, procaine, dibenzylammonium, or N-benzyl-β-phenethylammonium.

9. The derivative as set forth in claim 1 wherein the acyloxy is acetoxy.

10. The derivative as set forth in claim 1 wherein the aromatic heterocycle-thio group is 5-(1-methyltetrazolyl)thio or 2-(1,3,4-thiadiazolyl)thio.

11. The derivative as set forth in claim 1 wherein the aromatic nitrogen-containing heterocycle quaternary ammonium group is pyridinium, quinolinium, or picolinium.

12. The derivative as set forth in claim 1 wherein said derivative is α-[5-(4-methylphenyl)-3-isoxazolecarboxamido]benzylpenicillin, D-α-(5-phenylisoxazole-3-carboxamido)benzylpenicillin, D-α-(5-m-anisylisoxazole-3-carboxamido)benzylpenicillin, D-α-(5-m-nitrophenylisoxazole-3-carboxamidobenzylpenicillin, D-α-(5-p-methylphenylisoxazole-3-carboxamido)-p-hydroxybenzylpenicillin, D-α-[5-(2-pyridyl)isoxazole-3-carboxamido]benzylpenicillin, D-α-[5-(2-thienyl)isoxazole-3-carboxamido]benzylpenicillin, D-α-(5-m-chlorophenylisoxazole-3-carboxyamideobenzylpenicillin, D-α-(5-m-aminophenylisoxazole-3-carboxamido)benzylpenicillin, 7-β-[D(−)-α-(5-m-anizyl)isoxazole-3-carboxamido)-α-phenylacetoamideo]cephalosporanic acid, 7β-[D(−)-α-(5-(m-anisyl)isoxazole-3-carboxamido)-α-phenylacetamido]-3-(1-methyl-1H-tetrazole-5-yl)thiomethyl-3-cephem-4-carboxylic acid, 7β-(D(−)-α-(5-(2-thienyl)isoxazole-3-carboxamido)-α-phenylacetamideo]-3-acetoxymethyl-3-cephem-4-carboxylic acid and 7β-[D(−)-α-(5-(2-thienyl)isoxazole-3-carboxamido)-α-phenylacetamido]-3-(4-carbamoyl-pyridinium)methyl-3-cephem-4-carboxylate or a sodium salt thereof.

* * * * *